United States Patent [19]

Sundkvist et al.

[11] 3,999,438
[45] Dec. 28, 1976

[54] SAMPLING DEVICE

[75] Inventors: Gustaf Johannes Sundkvist, Skelleftehamn; Karl-Johan Bostrom, Skelleftea, both of Sweden

[73] Assignee: Boliden Aktiebolag, Stockholm, Sweden

[22] Filed: Dec. 17, 1975

[21] Appl. No.: 641,530

[30] Foreign Application Priority Data

Dec. 27, 1974 Sweden .............................. 7416316

[52] U.S. Cl. ............................................. 73/421 A
[51] Int. Cl.² ........................................... G01N 1/18
[58] Field of Search ...................... 73/421 A, 422 R

[56] References Cited

UNITED STATES PATENTS

| | | | |
|---|---|---|---|
| 1,964,775 | 7/1934 | Stuart | 73/421 A X |
| 2,670,629 | 3/1954 | Belden | 73/421 A |

*Primary Examiner*—Richard C. Queisser
*Assistant Examiner*—Joseph W. Roskos
*Attorney, Agent, or Firm*—Stevens, Davis, Miller & Mosher

[57] ABSTRACT

There is provided an apparatus for taking a sample-flow from a main suspension flow, said apparatus having a first chamber which is adapted to receive said main suspension flow and which communicates with a second chamber via weir means. The second chamber has at the lower portion thereof first and second opening means for dividing the suspension received from the first chamber into a sample-flow and a main residual flow, said first and second opening means communicating with a respective means for exerting on the suspension in the second chamber a counterpressure of such magnitude that the level of suspension therein is substantially the same as the level of suspension in the first chamber and that the speed at which the suspension flows into the first opening means is substantially equal to the speed at which the suspension flows into the second opening means.

8 Claims, 3 Drawing Figures

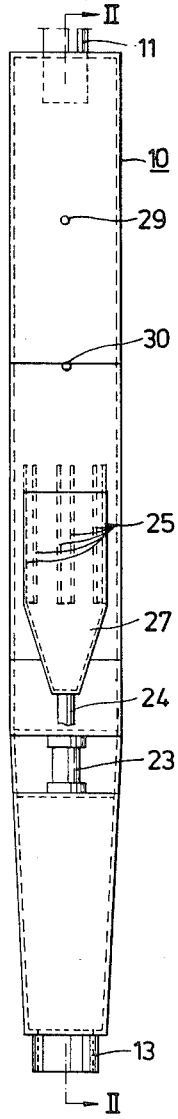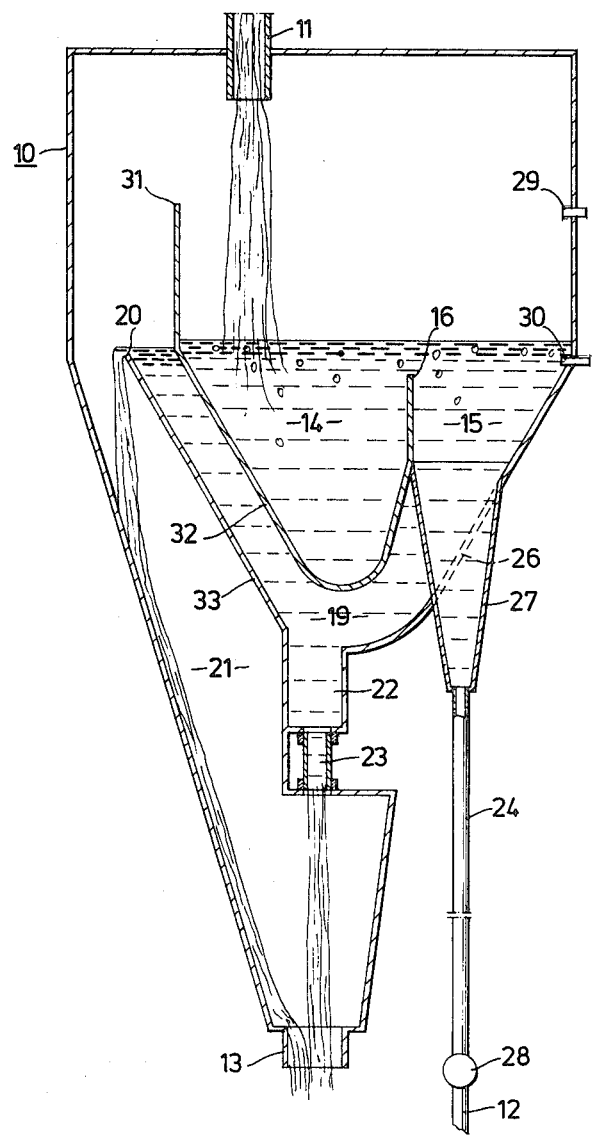

SAMPLING DEVICE

The present invention relates to an apparatus for taking from a flowing main liquid suspension of particles a sample-flow which is of constant flow rate and which is representative of the composition of said main suspension.

In order to be able to control effectively certain processes operating with flowing suspensions, such as flotation processes in enrichment plants, it must be possible to analyze the composition of the suspension flows quickly and continuously. The analyses can be carried out, for example, with the aid of X-rays, by taking representative sample flows from the main flows and passing each such sample flow through an associated measuring cell for continuous X-ray analysis, e.g. by means of the so-called pulp X-ray on stream technique.

From such an analysis, it is possible to obtain continuously information regarding the process in question on the basis of which information suitable measures for controlling the process can be undertaken. For optimal control, however, it is necessary that the sampling and analysis can be reliably effected. For example, with regard to the enrichment of ore a reliable, rapid and automatic direct analysis of the metal content of the particles suspended in the liquid is required, this analysis being effected, for example, with the aid of X-rays in a special measuring cell. At the same time as the metal content of the suspended particles is established in the analysis, the extent of dilution of the suspension is also determined, this being an important control parameter in ensuring that the enrichment process is effected satisfactorily.

In the present context, a measuring cell may comprise mainly a short vertical tube member through which the suspension sample-flow passes. Between the two ends of the tube member there is provided an opening which is covered with a thin membrane of synthetic resin material, through which the analysis with X-ray beams is effected. To ensure a positive and reliable analysis, it is necessary that the flow conditions and the pressure in the measuring cell are constant, so that the thin membrane constantly exhibits a substantially unchanged bulge-like configuration. It is also necessary with regard to the analysis that the pulp, i.e. the suspension sample-flow, is substantially free from gas bubbles.

A conventional method of taking a representative sample-flow is one in which one or more sampling slots are arranged in the path of a suspension flow which falls freely from a tube or over a weir, wherein said slot or slots completely traverse the flow of suspension and wherein, when more than one slot is used, said slots are mutually parallel. The rate of flow of the sample-flow removed through the slot or slots will, however, vary in step with variations of the main flow. With this conventional method of taking a sample-flow, it is impossible to obtain a sample-flow having a constant rate of flow and, at the same time, a composition which is representative of the flowing main suspension. Another disadvantage encountered with the removal of a sample-flow directly from a free-falling suspension in accordance with this conventional method is that air is readily sucked down into the sample-flow, as said flow enters the sampling slot or slots.

The removal of a sample-flow which is to be analyzed in a measuring cell, which cell requires constant pressure and a liquid which is free from gas bubbles, cannot therefore be effected from a free-falling suspension.

When handling suspensions containing heavy particles, which is particularly the case in enrichment processes, the pronounced tendency of the material to settle and to progressively form hard and difficultly removed coatings must always be taken into account. This undesirable sedimentation is normally avoided by agitating the suspension or by moving the suspension at a high speed of flow.

In certain instances, the suspension contains large quantities of dispersed air, as is the case with, for example, flotation enrichment. A conventional manner of ensuring that the liquid sample-flow is substantially free from dispersed air, is to permit the main flow to pass through a buffer tank, e.g. a so-called head tank. The main flow falls freely down into the tank and runs from said tank over a weir. A sample-flow is taken out through a separate opening arranged for this purpose in the bottom of the tank. The size of the tank in relation to the main flow is such that the residence time of the suspension in the tank is sufficient to enable practically all the dispersed air to depart from the region of the bottom of the tank, so that the sample-flow is free from dispersed air to the extent desired.

It has been found, however, that large differences in the contents and the extent of dilution of the suspension can exist between a sample-flow taken from the bottom of the tank and a major flow departing over a weir, owing to the fact that, inter alia, the different substances present in the suspension normally have mutually different particle densities. This is particularly true in the case of mineral ore contra waste material. Furthermore, the solid suspended material is present in different particle sizes which, similarly to the differences in density, give rise to different sedimentation rates. In certain instances, the sample-flow taken via the bottom outlet of the tank can be poorer in metal than the major flow which leaves the tank via the weir, owing to the fact that particles of mineral ore adhere to bubbles dispersed in the suspension and float with the bubbles and accompany the major flow.

It has now been found that these disadvantages can be least substantially eliminated by using an apparatus according to the present invention, said apparatus being mainly characterized in that it comprises a first chamber which is adapted to receive and to retard the flowing main suspension and which communicates via a weir with the upper portion of a second chamber having at least a first and at least a second opening arranged at the bottom thereof for removing said sample-flow and the remaining portion of the main suspension, respectively, said openings facing upwardly and extending transversely of the weir over the full width of the second chamber, and wherein the second opening communicates with an outlet via a means for subjecting the suspension flowing out through said second opening to a counterpressure of such magnitude that the level of the suspension in the second chamber is maintained in the region of the lip of the weir of the first chamber, while the first opening communicates with an outlet via a constriction which is so adapted that, with normal flow rate of the suspension entering the first chamber, the speed at which said suspension flows into the first opening is substantially equal to the speed at which the suspension flows into the second chamber and that any variations in pressure head in the second chamber caused by possible variations in the flow rate of the suspension entering the first chamber are insignificant in relation to the pressure drop over the constriction. By means of this arrangement there is obtained a quiet flow of suspension into and through the second chamber, and the sample taken is fully representative of said suspension at the same time as the flow rate of the sample is substantially constant, owing to the fact that the aforementioned variations in pressure head are small.

In accordance with a particularly preferred embodiment in which the level in the second chamber is maintained in a simple and reliable manner, the second opening communicates with the associated outlet via a second weir, the lip of which is located substantially on the same level as the lip of the weir of the first chamber, there being obtained particularly favourable flow conditions and constructive advantages when said communication is effected through a substantially U-shaped passage.

To avoid problems which result from sedimented material in the U-shaped passage according to the invention, there may be arranged in the lower portion of said passage an opening through which particles which may have settled in the passage can be removed, the area of said opening being so small as to ensure a constant flow of suspension over the second weir.

In accordance with the invention, the problem of gas dispersed in the suspension can be solved by ensuring that the dimensions of the second chamber are sufficient to permit gas dispersed in the suspension to depart therefrom prior to said suspension reaching the first and second openings.

One simple method of regulating the speed at which the sample-flow flows into said first opening so that said speed is equal to the speed at which the suspension flows into said second opening is to pass the sample-flow to its associated outlet via a downwardly extending pipe having a cross-sectional area and a length of such magnitude that the necessary throttling of said sample-flow is obtained.

The length of the pipe is suitably large in relation to the level variations which may occur in the second chamber and which can cause disturbing variations in the hydrostatic pressure. When the sample-flow passing through the pipe is analyzed while using a measuring cell mounted in the pipe, in order to avoid disturbance as a result of variations in hydrostatic pressure, the cell should be located at a distance beneath the level of liquid in the second chamber which distance is substantial in relationship with occurring level variations in the chamber.

To provide a compact apparatus which requires but a small amount of space, substantially all the components of the apparatus may be incorporated in a common casing. A particularly favourable construction is obtained when the first chamber is separated from the second chamber and the U-shaped passage by means of a U-shaped wall extending within the casing between two opposing walls thereof.

The invention will now be described in more detail with reference to an embodiment shown in the accompanying drawings, in which:

FIG. 2 is a vertical sectional view taken through the line II—II in FIG. 3;

FIG. 3 is a side view seen from the right of FIG. 2.

Figure 1:
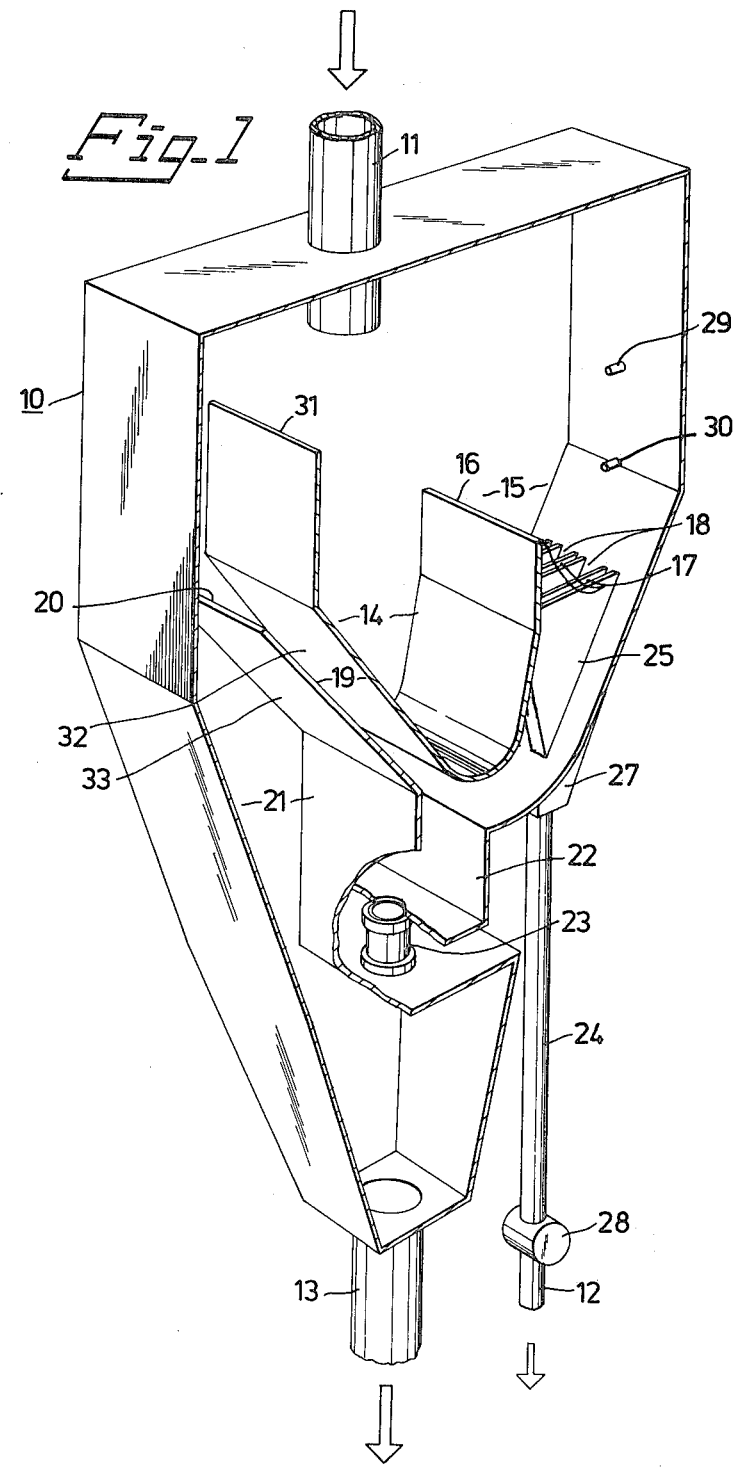
FIG. 1 is a perspective view of an apparatus according to the invention, in which parts have been cut away to show the construction more clearly.

The illustrated apparatus for removing from a flowing suspension, in the present case a flotation pulp containing air bubbles, a sample-flow which is of constant flow rate and which is representative of the composition of said suspension with the exception of its air-bubble content, comprises a casing, generally reference 10, having a suspension inlet 11 and first and second outlets 12 and 13 respectively for the sample-flow and the remainder of the suspension flow, respectively. Arranged in the casing 10 is a chamber 14 which receives the suspension entering through the inlet 11 and which is so constructed that it retards the suspension without promoting sedimentation of the suspended particles in the chamber. The suspension passes from the chamber 14 to a second chamber 15 via a weir 16.

The chamber 15 is provided in the vicinity of the bottom thereof with first and second openings 17 and 18 through which the sample-flow and the remaining portion of the suspension depart. Similar to the first chamber 14, the dimensions of the chamber 15 are sufficiently large to provide quiet flow conditions for the suspension which flows calmly over the weir 16. In this way, the air bubbles present in the incoming suspension are able to rise to the surface thereof and to depart, so that when the suspension reaches the openings 17, 18 it is substantially free from such air bubbles. The openings 17, 18 have the form of slots which extend transversely of the weir 16, the slots forming the sample-flow openings 17 being narrower than the slots forming the openings 18, so that the sample-flow is small in comparison with the flow passing through the openings 18, for example comprises 10–20% of the normal flow rate of the suspension entering through the inlet 11.

The openings 18 communicate with the outlet 13 through a means 19 which exerts a counterpressure on the suspension departing through the openings 18. More specifically, this suspension in the illustrated example passes into one leg of a U-shaped passage 19 and through said passage, the other leg of which forms at its upper end a weir 20 from which the suspension falls through a third chamber 21, formed in the casing 10, to the outlet 13. To prevent blocking of the U-shaped passage as a result of heavy material collecting in the lower portion thereof, said lower portion communicates directly with the chamber 21 via a collecting well 22 and a detachably mounted tube 23. The dimensions of the tube 23 are so small as to ensure a continuous flow of suspension over the weir 20, the lip of said weir 20 being located at such a height that the level of the suspension in the chamber 15 is maintained substantially on the same level as or slightly higher than the lip of the weir 16 of the chamber 14.

The first openings 17 communicate with the outlet 12 via a constriction 24. In the illustrated embodiment this constriction comprises a downwardly extending pipe of considerable length and is adjusted so that with a normal flow rate of the suspension entering through the inlet 11 the speed at which the suspension flows into the openings 17 is identical to the speed at which the suspension flows into the openings 18 and so that any variations in pressure head, caused by possible variations in the flow rate of the suspension entering through the inlet 11, are insignificant in relation to the drop in pressure over the constriction or pipe 24, for example of the order of magnitude of at most 5%, wherewith a constant or at least substantially constant flow rate is obtained in the pipe 24. Each of the openings 17 forms the mouth of a respective passage 25, which passages 25 may be exchangeable and which, at 26 (FIG. 2), discharge into a trough-like portion 27 to the underneath of which the pipe 24 is connected. Preferably, the pipe 24 is connected to the trough-like portion 27 so as to be readily removable therefrom, thereby enabling said pipe to be exchanged in full or in part so that the exact pressure drop desired in each particular case can be obtained. When the sample-flow passing through the pipe 24 is analyzed with the aid of a measuring cell mounted in the pipe, said cell being sensitive to variations in hydrostatic pressure, the measuring cell, which is indicated by the reference 28 in FIG. 2, should be located at a relatively large distance from the level of liquid in the chamber 15, as explained in the introduction.

If the level of the suspension in the chamber 15 varies excessively, for example as result of a blockage in the passage 19 or a halt in the supply of suspension through the inlet 11, so that the sample-flow, despite the provision of the passage 19 and the constriction 24, no longer is of substantially constant flow rate nor representative of the composition of the suspension entering through the inlet 11, it is important that this is brought to the attention of the supervising personnel. To this end there can be provided, as shown at 29 and 30, level sensors which give a signal or which react in some other suitable manner in dependence upon the applied process control when the level of the suspension in the chamber 15 is impermissably high or low. When the level of the suspension in the chamber 15 is too high, the suspension flowing through the inlet 11 may be caused to flow directly to the outlet 13 via a weir 31 formed by an upstanding wall portion and the chamber 21.

In the illustrated embodiment, the different chambers and passages are delimited with the aid of the casing 10 and plates or the like mounted therein so as to obtain a compact construction which requires but little space. Thus, the plate 32 forms simultaneously a partition between the chambers 14 and 15, a partition between the chamber 14 and the passage 19, the weir 16 and the weir 31, while the plate 33 forms simultaneously the weir 20, a partition between the chamber 21 and the passage 19 and a partition between the passage 19 and the collecting well 22.

The invention is not restricted to the aforedescribed and illustrated embodiment, but can be modified within the scope of the following claims.

We claim:
1. An apparatus for taking from a flowing main liquid suspension of particles a sample-flow which is of constant flow rate and which is representative of the composition of said main suspension, characterized in that said apparatus comprises a first chamber which is adapted to receive and to retard the flowing main suspension and which communicates via a weir with the upper portion of a second chamber having at least a first and at least a second opening arranged at the bottom thereof for removing said sample-flow and the remaining portion of the main suspension, respectively, said openings facing upwardly and extending transversely of the weir over the full width of the second chamber, and wherein the second opening communicates with a first outlet via a means for subjecting the suspension flowing out through said second opening to a counterpressure of such magnitude that the level of the suspension in the second chamber is maintained in the region of the lip of the weir of the first chamber, while the first opening communicates with a second outlet via a constriction which is so adapted that, with normal flow rate of the suspension entering the first chamber, the speed at which said suspension flows into the first opening is substantially equal to the speed at which the suspension flows into the second opening and that any variations in the pressure head in the second chamber caused by possible variations in the flow rate of the suspension entering the first chamber are insignificant in relation to the pressure drop over the constriction.

2. An apparatus according to claim 1, characterized in that the second opening communicates with said first outlet via a second weir, the lip of which is located substantially on the same level as the lip of the weir of the first chamber.

3. An apparatus according to claim 2, characterized in that the second opening is connected with the second weir via a substantially U-shaped passage.

4. An apparatus according to claim 3, characterized by a third opening arranged in the lower portion of the U-shaped passage and intended for the removal of particles which may have settled in the passage and the cross-sectional area of the third opening is so small that a constant flow over the second weir is ensured.

5. An apparatus according to claim 1 characterized in that the dimensions of the second chamber are sufficient to permit gas dispersed in the suspension to depart therefrom prior to said suspension reaching said first and second openings.

6. An apparatus according to claim 1 characterized in that the first opening communicates with said second outlet via a downwardly extending pipe of considerable length in relation to variations occurring in the level of the suspension in the second chamber.

7. An apparatus according to claim 3 characterized in that substantially all the components of said apparatus are incorporated in a common casing.

8. An apparatus according to claim 7, characterized in that the first chamber is delimited from the second chamber and the U-shaped passage by means of a U-shaped wall extending within the casing between two opposing walls thereof.

* * * * *